US012622890B2

(12) United States Patent
Lu et al.

(10) Patent No.: US 12,622,890 B2
(45) Date of Patent: May 12, 2026

(54) USE OF THE ACTIVE COMPOUND IN THE PREVENTION OR TREATMENT OF OVARIAN DYSFUNCTION DISEASES

(71) Applicant: INSTITUTE OF BIOPHYSICS, CHINESE ACADEMY OF SCIENCES, Beijing (CN)

(72) Inventors: Cuiling Lu, Beijing (CN); Tao Jiang, Beijing (CN); Yanxiao Yi, Beijing (CN)

(73) Assignee: Institute of Biophysics, Chinese Academy of Sciences, Beijing (CN)

(*) Notice: Subject to any disclaimer, the term of this patent is extended or adjusted under 35 U.S.C. 154(b) by 408 days.

(21) Appl. No.: 18/267,003

(22) PCT Filed: Sep. 2, 2022

(86) PCT No.: PCT/CN2022/116863

§ 371 (c)(1),
(2) Date: Jun. 13, 2023

(87) PCT Pub. No.: WO2023/206903

PCT Pub. Date: Nov. 2, 2023

(65) Prior Publication Data

US 2024/0390314 A1 Nov. 28, 2024

(30) Foreign Application Priority Data

Apr. 27, 2022 (CN) ......................... 202210453982.4

(51) Int. Cl.
*A61K 31/225* (2006.01)
*A61K 31/575* (2006.01)
(Continued)

(52) U.S. Cl.
CPC .......... *A61K 31/225* (2013.01); *A61K 31/575* (2013.01); *A61P 5/24* (2018.01); *A61P 15/08* (2018.01); *A61P 39/06* (2018.01)

(58) Field of Classification Search
CPC ...... A61K 31/225; A61K 31/575; A61P 15/08
See application file for complete search history.

(56) References Cited

U.S. PATENT DOCUMENTS

2017/0056356 A1 3/2017 Rajasekhar
2021/0283089 A1 9/2021 Chen et al.

FOREIGN PATENT DOCUMENTS

WO 2010069139 A1 6/2010
WO WO-2016074684 A1 * 5/2016 ........... A61K 38/482
WO 2023206903 A1 11/2023

OTHER PUBLICATIONS

Sehayek et al., J. Lipid Res. 2001. 42: 1250-1256 (Year: 2001).*
International Search Report and Written Opinion for application No. PCT/CN2022/116863 dated Jan. 18, 2023.

* cited by examiner

*Primary Examiner* — San Ming R Hui
(74) *Attorney, Agent, or Firm* — DLA Piper LLP

(57) ABSTRACT

Use of the active compound in the present disclosure for the prevention or treatment of ovarian dysfunction disease. In particular, the present disclosure relates to the use of a compound shown in Formula I or a pharmaceutically acceptable salt thereof in the treatment or prevention of ovarian dysfunction disease, wherein R1 and R2 are each independently selected from H, C1-C6 alkyl, C1-C6 alkenyl, and C1-C6 alkynyl. The present disclosure also relates to the use of a compound shown in said Formula I or a pharmaceutically acceptable salt thereof, in combination with hyodeoxycholic acid or a pharmaceutically acceptable salt thereof, in the treatment or prevention of ovarian dysfunction disease. The present disclosure also relates to compositions comprising a compound shown in said Formula I or a pharmaceutically acceptable salt thereof and/or hyodeoxycholic acid or a pharmaceutically acceptable salt thereof.

(Continued)

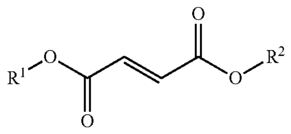
Formula I
13 Claims, 12 Drawing Sheets
(51) Int. Cl.
*A61P 5/24* (2006.01)
*A61P 15/08* (2006.01)
*A61P 39/06* (2006.01)

scale: 50μm

USE OF THE ACTIVE COMPOUND IN THE PREVENTION OR TREATMENT OF OVARIAN DYSFUNCTION DISEASES

This application is the National Stage filing under 35 U.S.C. 371 of International Application No. PCT/CN2022/116863, filed Sep. 2, 2022, which claims the benefit of Chinese Provisional Application No. 202210453982.4, filed Apr. 27, 2022. The disclosures of each of these applications are incorporated herein by reference.

TECHNICAL FIELD

The invention relates to methods and drugs for preventing or treating ovarian dysfunction diseases.

BACKGROUND OF THE INVENTION

The ovary is an important reproductive and endocrine organ of female animals. Its functions include ovulation and secretion of hormones (such as steroid hormones, estrogen and progesterone). When the ovarian function is dysregulated, such as abnormal follicle maturation or reduced secretion of steroid hormones, a series of ovarian dysfunction diseases will be triggered, such as follicle development, maturation or ovulation failure, patients may suffer from infertility, spontaneous abortion and premature senescence, and also affect the endocrine function of the ovary.

At present, hormone replacement therapy and assisted reproduction therapy are the main treatments of ovarian dysfunction diseases. Hormone replacement therapy can effectively improve estrogen and serum FSH level in short-term, but with more side effects and contraindications, such as gastrointestinal discomfort, weight gain, increased risk of endometrial cancer, breast cancer and other gynecological cancers. Use of estrogen can also increase the risk of venous thrombosis with poor long-term curative effect. At the same time, clinically, patients have a certain psychological burden for hormone therapy or refuse to use hormone therapy. Assisted reproductive therapy, is expensive and mostly unavailable for patients who are anovulation or ovulating sparsely. Importantly, there are no clear and effective strategies to prevent and delay ovarian dysfunction diseases.

Therefore, it is urgent to find a new drug with obvious effect and low side effects for the prevention or treatment of ovarian dysfunction diseases.

THE INVENTION CONTENTS

To address one of the above technical problems, this disclosure provided drugs and methods for the treatment or prevention of ovarian dysfunction diseases. After treatment with drugs in this disclosure, ovarian function can be effectively restored, and follicle development and ovulation can be promoted.

According to one aspect of this disclosure, the application of the compounds shown in Formula I or their pharmaceutically acceptable salts in the treatment or prevention of ovarian dysfunction diseases is provided, Formula I

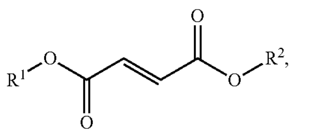

Among them, R1 and R2 are each independently selected from H, C1-C6 alkyl group, C1-C6 alkenyl group and C1-C6 alkyne group.

According to some embodiments, R1 and R2 can be each independently selected from H.

According to some embodiments, R1 and R2 can be each independently selected from branched or straight chain C1-C6 alkyl groups. According to specific embodiments, R1 and R2 can be each independently selected from branched or straight chain C1-C5 alkyl groups. According to specific embodiments, R1 and R2 can be each independently selected from branched or straight chain C1-C4 alkyl groups. According to specific embodiments, R1 and R2 can be each independently selected from branched or straight chain C1-C3 alkyl groups. According to specific embodiments, R1 and R2 can be each independently selected from methyl, ethyl, n-propyl, isopropyl, n-butyl, sec-butyl, tert-butyl, or n-pentyl groups.

According to some embodiments, R1 and R2 can be each independently selected from the branched or straight chain C1-C6 alkenyl groups. According to specific embodiments, R1 and R2 can be each independently selected from the branched or straight chain C1-C5 alkenyl groups. According to specific embodiments, R1 and R2 can be each independently selected from branched or straight chain C1-C4 alkenyl groups. According to specific embodiments, R1 and R2 can be each independently selected from branched or straight C1-C3 alkenyl groups. According to specific embodiments, R1 and R2 can be each independently selected from vinyl, propylene, butenyl, or pentenyl groups.

According to some embodiments, R1 and R2 can be each independently selected from branched or straight C1-C6 alkynyl groups. According to specific embodiments, R1 and R2 can be each independently selected from the branched or straight C1-C5 alkyne group. According to specific embodiments, R1 and R2 can be each independently selected from branched or straight C1-C4 alkyne groups. According to specific embodiments, R1 and R2 can be each independently selected from branched or straight C1-C3 alkyne groups. According to specific embodiments, R1 and R2 can be each independently selected from acetylene, propylene, or butyne groups.

According to some embodiments, R1 and R2 can be the same or different.

According to some embodiments, the ovarian dysfunction diseases may include, but are not limited to, premature ovarian insufficiency (POI), premature ovarian failure (POF), diminished ovarian reserve (DOR), poor ovarian response (POR), early menopause, impaired ovarian function, insufficient ovarian function and lowered ovarian function. The ovarian dysfunction diseases may be caused by genetic factors, iatrogenic factors, immunologic factors, environmental factors, physical advanced age or other factors. The ovarian dysfunction diseases may appear hormone secretion disorder, menstrual (estrous) cycle disorder, rare ovulation or non-ovulation and other symptoms, can cause reproductive function decline, infertility, perimenopausal syndrome, menopause syndrome and other diseases.

According to specific embodiments, the ovarian dysfunction disease is premature ovarian insufficiency (POI).

According to specific embodiments, the ovarian dysfunction disease is diminished ovarian reserve (DOR). According to specific embodiments, the ovarian dysfunction disease is premature ovarian failure (POF).

According to specific embodiments, the ovarian dysfunction disease is poor ovarian response (POR). According to specific embodiments, the ovarian dysfunction disease is early menopause.

According to specific embodiments, the ovarian dysfunction disease is impaired ovarian function. According to specific embodiments, the ovarian dysfunction disease is insufficient ovarian function. According to specific embodiments, the ovarian dysfunction disease is lowered ovarian function.

According to some embodiments, the compound shown in Formula I or its pharmaceutically acceptable salt may be used in combination with byodeoxycholic acid or its pharmaceutically acceptable salt.

According to some embodiments, the compound shown in Formula I or its pharmaceutically acceptable salt alone or in combination with hyodeoxycholic acid may reduce serum levels of follicle-stimulating hormone (FSH) and increase levels of estrogens (e.g., estradiol), thus treat or prevent ovarian dysfunction.

According to some embodiments, the compound shown in Formula I or its pharmaceutically acceptable salt alone or in combination with hyodeoxycholic acid may alleviate oxidative stress damage. According to specific embodiments, the compound shown in Formula I or its pharmacologically acceptable salt alone or in combination with hyodeoxycholic acid can increase the level of superoxide dismutase (SOD) and decrease the level of malondialdehyde (MDA) and reactive oxygen species (ROS) in serum. This can improve the body's antioxidant capacity, reduce the degree of oxidative stress, thereby preventing or treating ovarian dysfunction.

According to some embodiments, the compound shown in Formula I or its pharmaceutically acceptable salt alone or in combination with hyodeoxycholic acid may restore ovulation in subjects with ovarian disorders.

According to another aspect, a composition is provided for the prevention or treatment of ovarian disorders, including the compound indicated in Formula I or its pharmaceutically acceptable salt, and/or hyodeoxycholic acid and its pharmaceutically acceptable salt.

Formula I

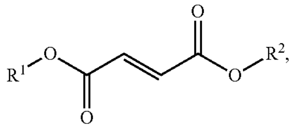

Among them, R1 and R2 are each independently selected from H, C1-C6 alkyl group, C1-C6 alkenyl group and C1-C6 alkyne group.

For the compounds shown in Formula I, R1 and R2 are defined as above.

According to some embodiments, the composition includes the compound shown in Formula I and its pharmaceutically acceptable salt, and hyodeoxycholic acid and its pharmaceutically acceptable salt, The mass ratio of the compound shown in Formula I and its pharmaceutically acceptable salt to hyodeoxycholic acid and its pharmaceutically acceptable salt is 10:1-1:10.

According to some embodiments, the composition further includes pharmaceutically acceptable excipients. According to some embodiments, the pharmaceutically acceptable excipients may include, but are not limited to, one or more of pharmaceutical carriers, diluents, adjuvants, and excipients.

According to some embodiments, the dosage forms of the composition include, but are not limited to, tablets, capsules, solutions, granules, pills, powders, ointments, elixirs, suspensions, dust, injections, suppositories, creams, sprays, patches, sustained release preparations, controlled release preparations or targeted preparations.

According to some embodiments, the composition may be administered, for example, by injection, oral, rectal administration, etc.

According to some embodiments, the compounds indicated in Formula I and their pharmaceutically acceptable salts, and/or hyodeoxycholic acid and their pharmaceutically acceptable salts are formulated to be applied in the same dosage form or in separate dosage forms.

According to another aspect, a method is provided for the treatment or prevention of ovarian dysfunction disease involving the administration to subjects in need of a therapeutic effective amount of the compound indicated in Formula I and its pharmaceutically acceptable salt, and/or hyodeoxycholic acid and its pharmaceutically acceptable salt.

According to some embodiments, the method includes simultaneous or sequential application of the compound indicated in Formula I and its pharmaceutically acceptable salt, and hyodeoxycholic acid and its pharmaceutically acceptable salt.

The inventors of this disclosure found that levels of some metabolites, such as fumaric acid and hyodeoxycholic acid in the serum of patients with ovarian dysfunction, was significantly reduced by comparing the fasting serum of patients with ovarian dysfunction with that of healthy persons (controls). In this disclosure, using mice model of premature ovarian failure, it was further verified that the fumaric acid and its derivatives alone or in combination with hyodeoxycholic acid orally lavaged for only 12 days, can reduce levels of follicle-stimulating hormone, increase levels of estrogen, and reduce levels of oxidative stress, significantly increase numbers of ovarian follicle at all levels (primitive, primary, secondary, mature follicle) and corpus luteum, and reduce the number of atretic follicles in mice. In addition, the number of estrous cycle recovery mice was significantly increased compared with the control group, and the data of serum detection showed that the antioxidant index was improved in treatment group. These results indicate that fumaric acid and its derivatives alone or in combination with byodeoxycholic acid have significant therapeutic effects on ovarian dysfunction diseases.

In prior art, estrogen drugs are usually used to treat ovarian dysfunction diseases, but estrogen has the following side effects. First of all, estrogen will stimulate endometrial lesions. Female estrogen, androgen, progesterone are mutual effect or interaction. If estrogen is secreted too much under the action of drugs and pituitary gland, the endometrium will be hyperplasia under the action of estrogen for a long time, thus causing the lesion of the endometrium. Secondly, long-term exposure of uterine to estrogen will lead to uterine fibroids, and the breast disease will also occur under the action of estrogen, leading to breast hyperplasia and even breast cancer. In addition, estrogen will also affect the central nervous system of the human body, taking too much estrogen will lead to dizziness, nausea, and even lead to hypertension, diabetes and so on. In this disclosure, fumaric acid itself is a precursor of L-malate in the tricarboxylic acid cycle (TCA), formed by the oxidation of succinate by succinate dehydrogenase, and hyodeoxycholic acid is also a naturally occurring bile acid. Therefore, the use of these two naturally occurring substances in the body to treat ovarian disorders will not produce adverse reactions, which is safer with minor side effect.

DESCRIPTIONS OF THE DRAWINGS

FIG. 2A shows the weight changes of mice before modeling, after modeling and after treatment in each group, and FIG. 2B shows the weight changes of mice before modeling, after modeling and after treatment in each group.

Figure 4:
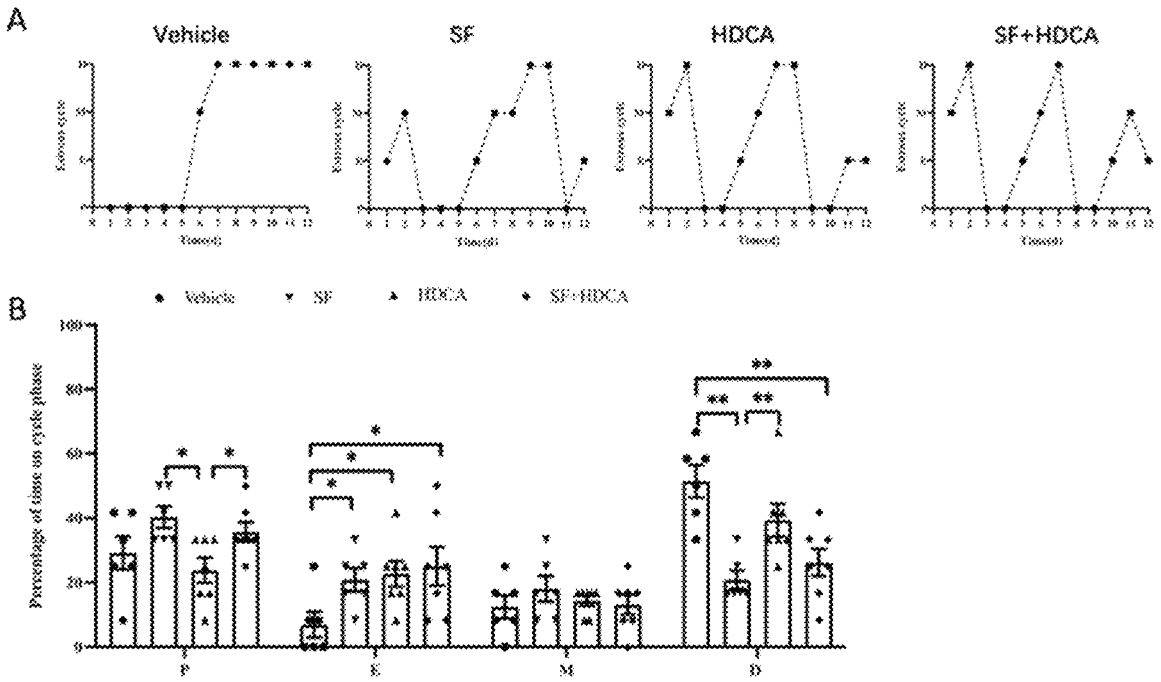

FIG. 4 shows the results of estrous cycle detection in mice according to one embodiment. FIG. 4A shows the representative estrous cycle of mice in Example 1. FIG. 4B shows the proportion of each period of the estrous cycle of each group of mice during administration in Example 1. * indicates significant difference ($P<0.05$); ** indicates significant difference ($P<0.01$).

Figure 5:
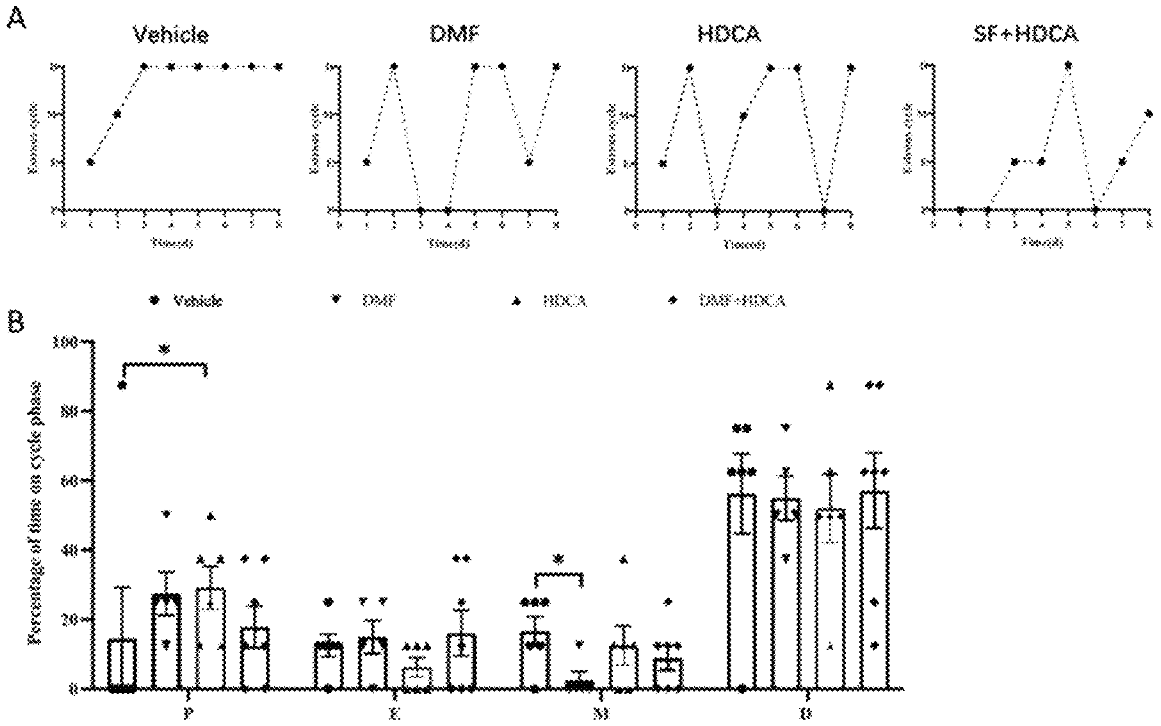

FIG. 5 shows the results of estrous cycle detection in mice according to one embodiment. FIG. 5A is the representative estrous cycle diagram of Example 2. FIG. 5B shows the proportion of each period of the estrous cycle of each group of mice during administration in Example 2. * indicates significant difference ($P<0.05$); ** indicates significant difference ($P<0.01$).

Figure 6:
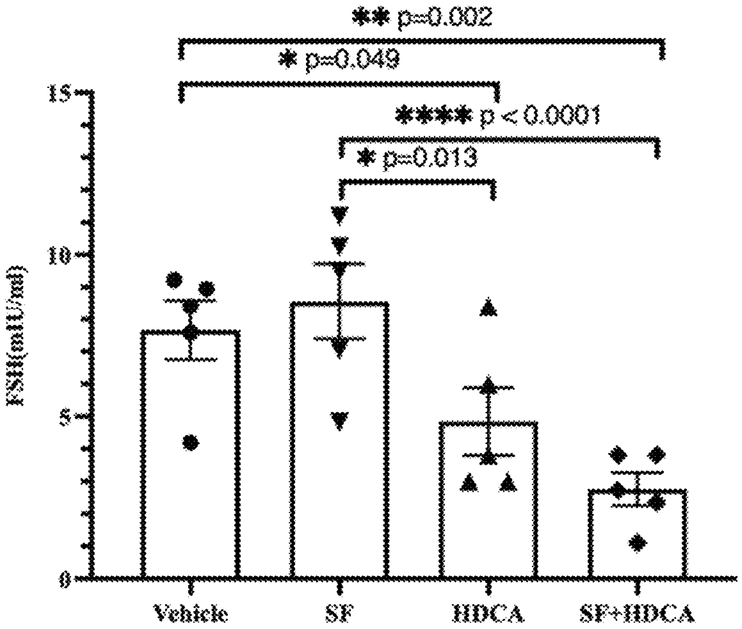

FIG. 6 shows the serum FSH levels of each group of mice after administration according to one embodiment. * indicates significant difference ($P<0.05$).  indicates significant difference ($P<0.01$): ** indicates significant difference ($P<0.0001$).

Figure 7:
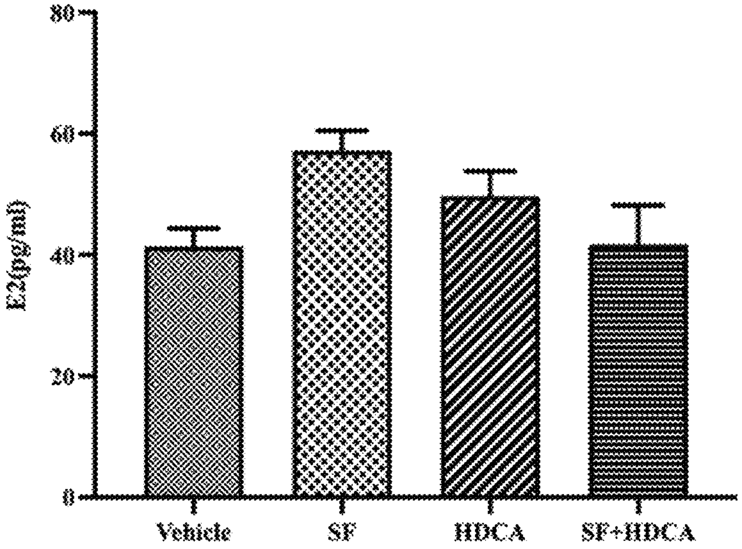

FIG. 7 shows the serum estradiol (E2) levels in each group of mice after administration according to one embodiment.

Figure 8:
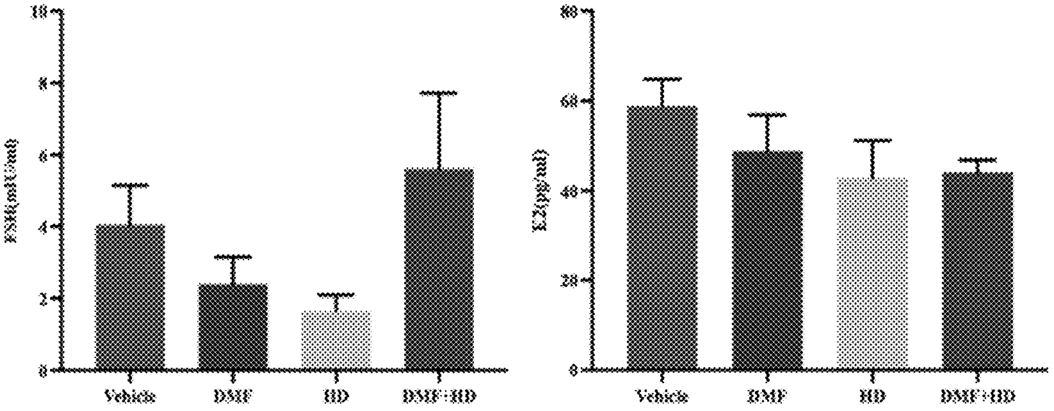

FIG. 8 shows the levels of serum FSH and serum estradiol (E2) in each group of mice after administration according to one embodiment.

Figure 9:
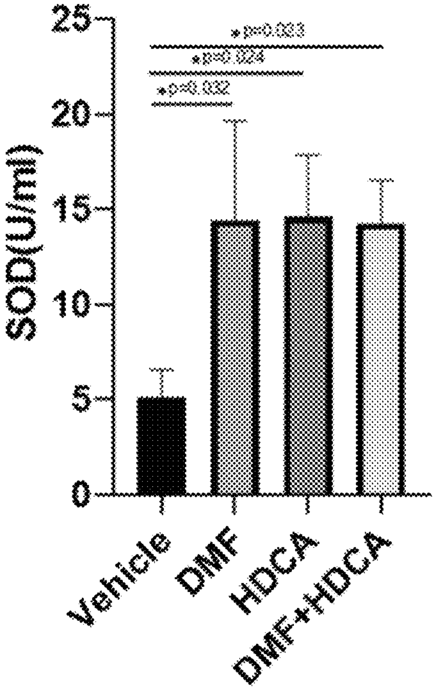

FIG. 9 shows the serum superoxide dismutase (SOD) levels after administration of mice in each group according to one embodiment.

Figure 10:
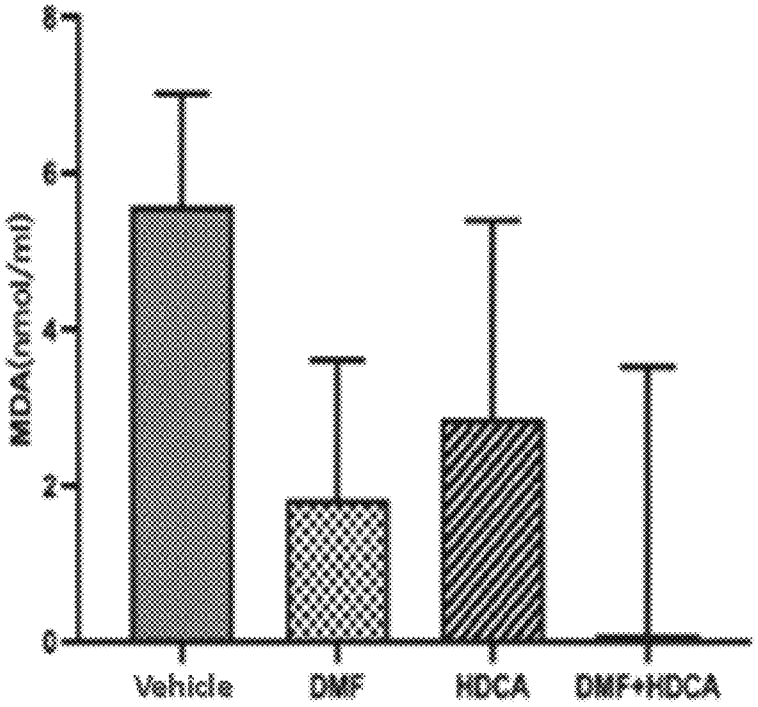

FIG. 10 shows the serum malondialdehyde (MDA) levels in each group of mice after administration according to one embodiment.

Figure 11:
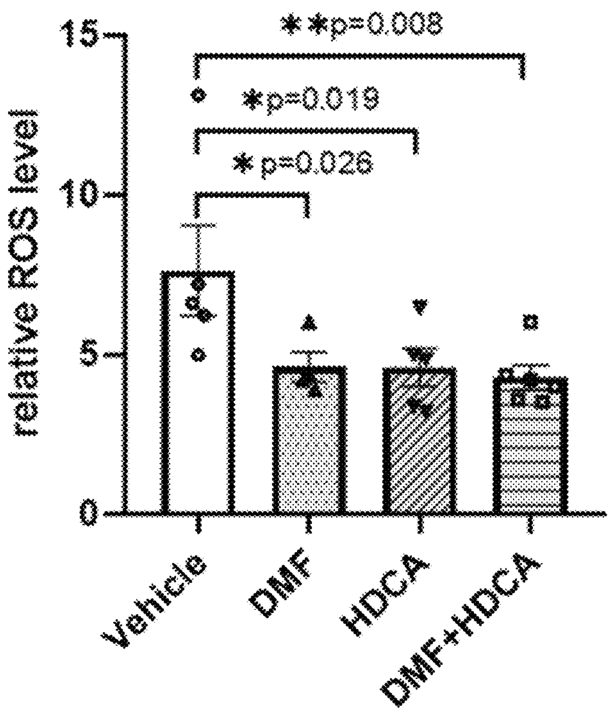

FIG. 11 shows the levels of reactive oxygen species (ROS) after administration in each group of mice according to one embodiment.

Figure 12:
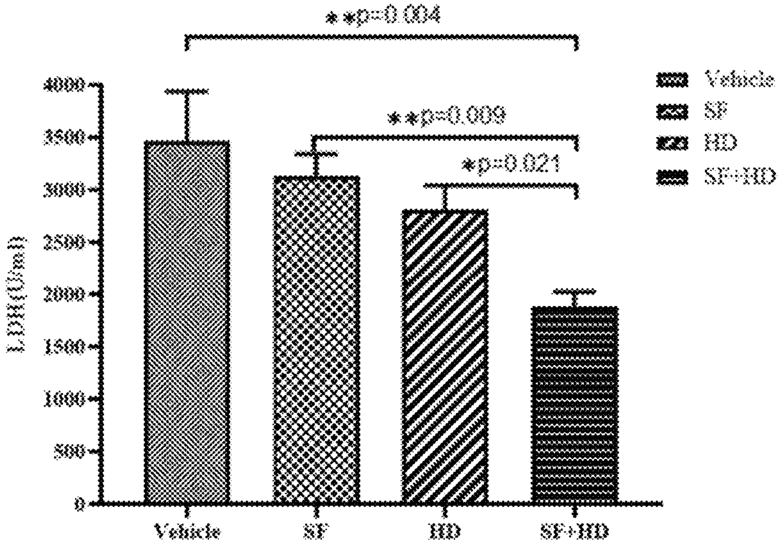

FIG. 12 shows the serum lactate dehydrogenase (LDH) levels in each group of mice after administration according to one embodiment.

Figure 13:
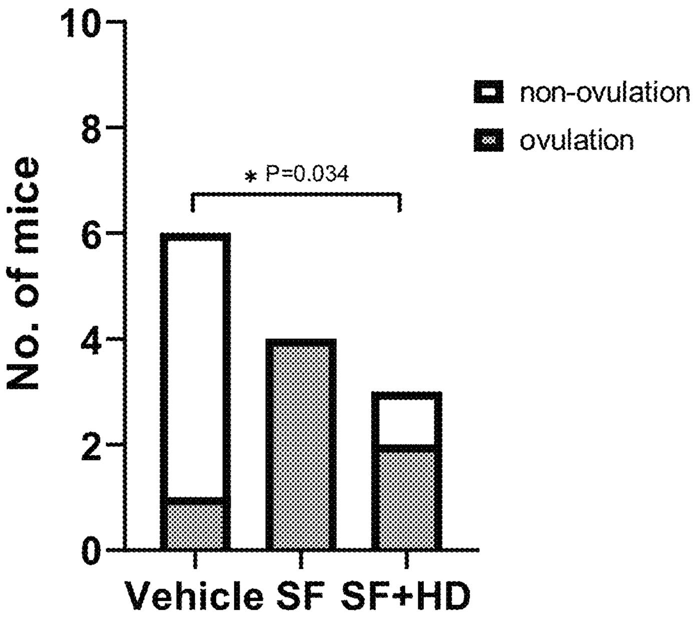

FIG. 13 shows the effect of administration on the number of oocytes obtained in mice according to one embodiment.

Figure 14:
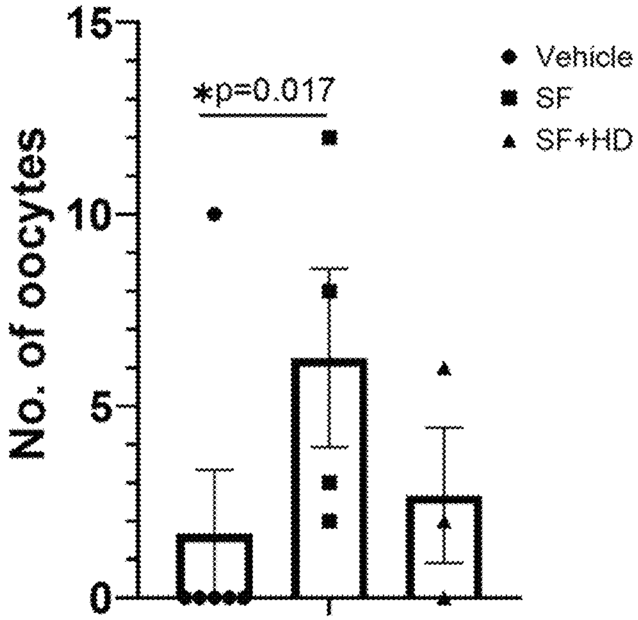

FIG. 14 shows the effect of administration on the number of oocytes obtained in mice of diminished ovarian function according to one embodiment.

Figure 15:
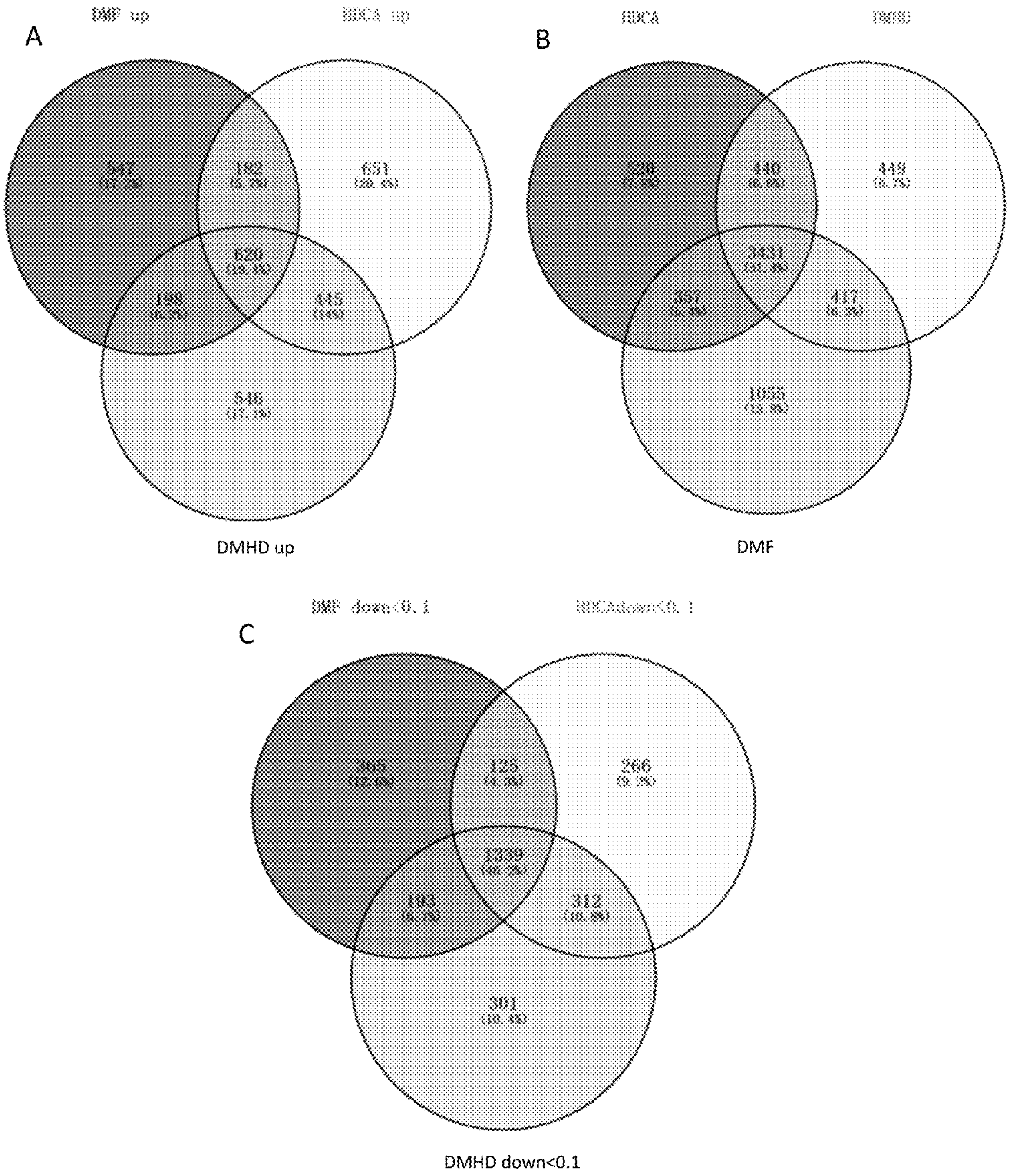

FIG. 15 shows the differential expression genes of the three treatment groups compared with the control group and the three-group intersection diagram according to one embodiment. FIG. 15A: The number and proportion of up-regulated genes in the three treatment groups; FIG. 15B: The number and proportion of down-regulated genes in the three treatment groups; FIG. 15C: The number and proportion of down-regulated genes in the three treatment groups.

Figure 16:
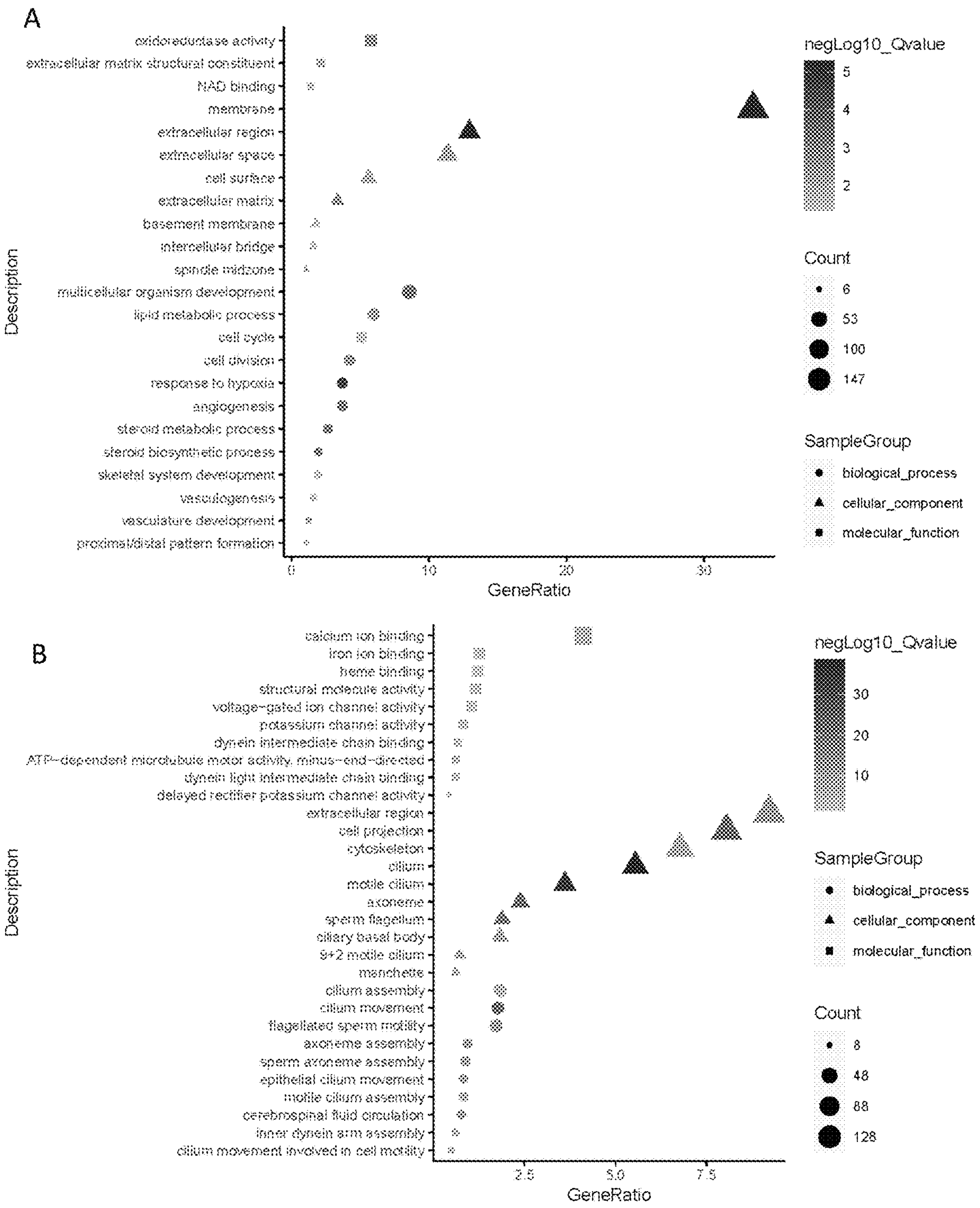

FIG. 16 shows the functional enrichment map of the differential genes commonly up-regulated or down-regulated in the three treatment groups according to one embodiment ($p<0.05$ for Top10). FIG. 16A: Functional enrichment map of genes commonly up-regulated in the three treatment groups; FIG. 16B: Functional enrichment map of genes commonly down-regulated in the three treatment groups.

Figure 17:
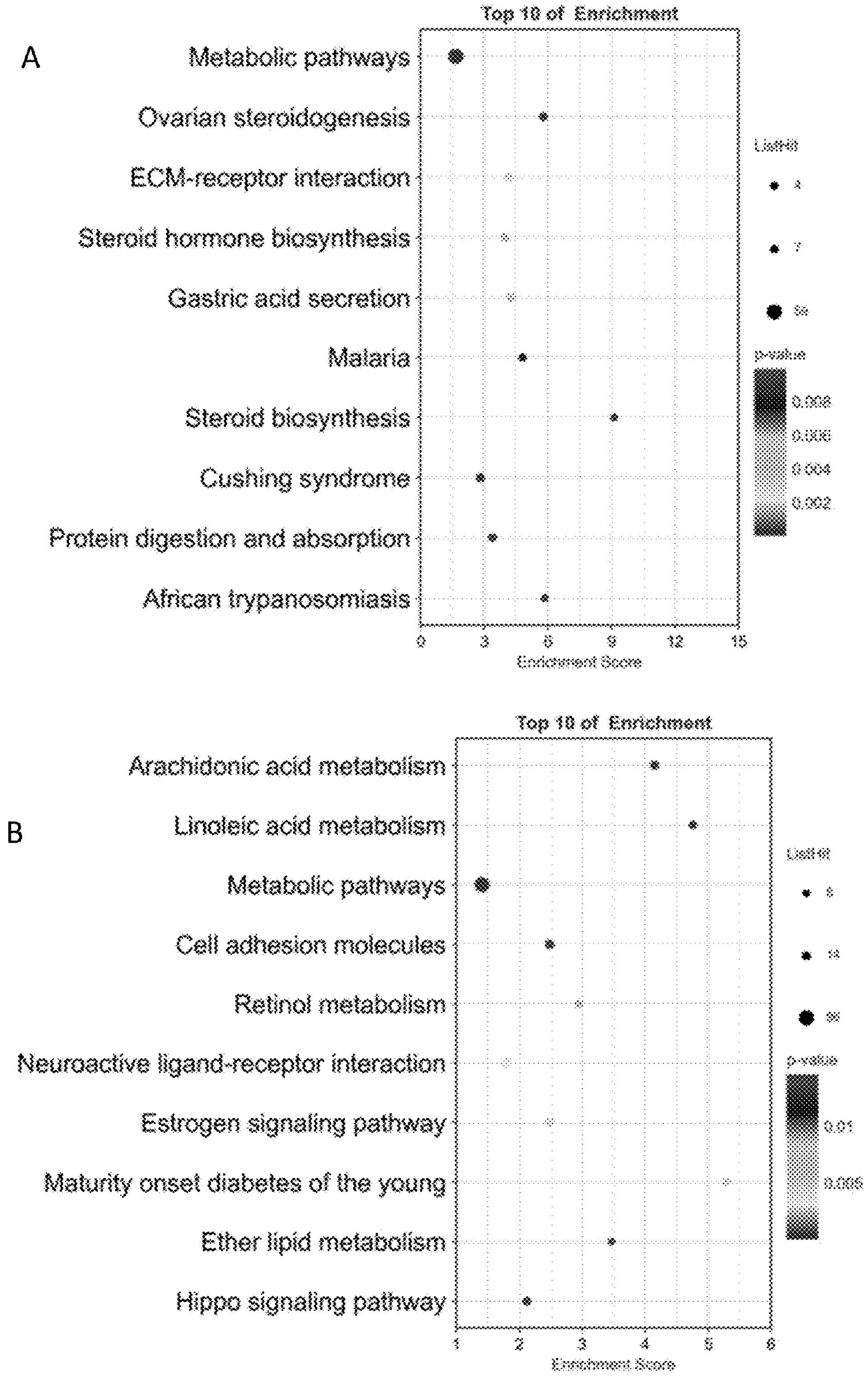

FIG. 17 shows the signaling pathways enrichment map of differential genes commonly up-regulated or down-regulated in the three treatment groups according to one embodiment ($p<0.05$ for Top10). FIG. 17A: KEGG (Kyoto Encyclopedia of Genes and Genomes) map of the commonly up-regulated 2-fold express genes in the three treatment groups; FIG. 17B: KEGG map of the commonly down-regulated 10-fold express genes in the three treatment groups.

SPECIFIC EMBODIMENTS

In order to make the purpose, technical solutions and advantages of the invention more clear, the invention is further explained in detail in the following combined with embodiments. The specific embodiments described herein are intended only to interpret the invention and are not intended to constitute any limitation of the invention. In addition, in the following descriptions, the description of public knowledge structures and techniques is omitted to avoid unnecessary confusion of the available concepts in this disclosure. Such structures and techniques have also been described in many publications.

DEFINITION

Unless otherwise defined, all technical terms and technological terms used in the invention have the same meaning as would normally be used in the field to which the invention belongs. For the purpose of interpreting this specification, the following definitions will be applied and, where appropriate, terms used in the singular will also include the plural and vice versa.

The expressions "one kind" and "single" used herein include the plural unless the context expressly states otherwise. For example, a reference to "a cell" includes multiple such cells and equivalents known to a technician in the field, etc.

The term "about" used herein denotes a range of ±20% of the value that follows. In some embodiments, the term "about" means a range of ±10% of the value that follows. In some embodiments, the term "about" means a range of ±5% of the value that follows.

The term "premature ovarian insufficiency (POI)" used herein is a severe ovarian dysfunction disease, which refers to the loss of ovarian function in women due to follicle depletion before the age of 40. The clinical manifestations were amenorrhea, sporadic menstruation or frequent menstruation lasting for 4 months, follicle stimulating hormone (FSH) more than 25 U/L tested twice for more than 4 weeks apart, with or without fluctuating decrease in estrogen level. Long-term risks include congenital heart disease, intellectual disability, mood disorders, osteoporosis, adrenal or thyroid underfunction, diabetes, and recurrent miscarriage, etc. POI patients suffer from severe ovulation dysfunction due to ovarian function decline, and significant fertility decline or loss. The incidence of POI is as high as 10-28% in patients with primary amenorrhea, and the overall incidence is about 3.7%, with an increasing trend year by year. Clinically, POI patients may present with primary amenorrhea or even pubertal development loss. Most of them are secondary amenorrhea, which is caused by natural aging, chromosomal or genetic defects, autoimmune diseases, environmental factors and iatrogenic factors, etc.

The term "premature ovarian failure (POF)" used herein refers to a woman who has amenorrhea for more than 4 to 6 months before the age of 40, with follicle stimulating hormone (FSH) more than 40 U/L tested twice for more than 4 weeks apart, accompanied by estrogen reduction and menopausal symptoms. Premature ovarian failure is one of the main causes of female infertility. According to the American Society for Reproductive Medicine, FSH level, fertility and menstruation were used as parameters, and the disease process was divided into normal, occult, biochemical abnormality and clinical abnormality stages.

The term "ovarian reserve" used herein refers to the primordial follicles contained in a woman's ovarian cortex. After birth, the number of primordial follicles does not increase, and the number of primordial germ cells in the ovarian cortex does not increase. Diminished/decreased ovarian reserve (DOR), also known as diminished ovarian reserve function, decreased ovarian reserve function, diminished ovarian reserve, decreased ovarian reserve, etc., refers to the number of follicles in the ovary is less than the expected number of follicles, decreased ovarian responsiveness and fecundity in women of reproductive age. This can make conception more difficult and reduce the chances of undergoing in vitro fertilization (IVF) and other fertility treatments. Patients with DOR also have a higher chance of miscarriage than women without DOR. Patients with DOR have decreased oocyte number and/or quality in the ovary, accompanied by increased FSH levels.

The term "early menopause" used herein refers to the onset of menopause earlier than the normal age of menopause, before the age of 45.

The term "poor ovarian response (POR)" used herein, also known as low ovarian response, refers to the low ovarian response to stimulating drugs and low number of oocytes retrieved when women received controlled ovarian hyperstimulation by assisted reproductive technology. POR is considered to be an early sign of decreased ovarian reserve.

The term gonadotrophin (Gn) used herein is a glycoprotein hormone that regulates the development of the vertebrate gonad and promotes the production and secretion of sex hormones. For example, the luteinizing hormone (LH) and follicle-stimulating hormone (FSH) secreted by the anterior pituitary gland act synergistically to stimulate the development of germ cells and the production and secretion of sex hormones in the ovary or testis. The human placenta secretes chorionic gonadotropin (HCG), which can promote the secretion of progesterone by the corpus luteum during pregnancy.

The term "estrogen" used herein is mainly secreted by the ovary, mainly including estradiol (E2), estrone, estriol and so on. Estrogen can promote the development and maturation of the accessory reproductive organs, vagina, uterus and oviduct of adolescent girls. Estradiol itself is a steroidal estrogen secreted by granulosa cells of ovarian follicles. There are two types of estradiol: α and β. The physiological effect of α E2 is stronger. In patients with premature ovarian failure, E2 levels decline.

The term "follicle-stimulating hormone (FSH)" used herein refers to a heterodimeric glycoprotein hormone secreted by the anterior pituitary basophils, which consists of different subunits α and β. It regulates human growth, development, pubertal sexual maturation, and a series of physiological processes related to reproduction through the female hypothalamic-pituitary-ovarian axis. FSH is secreted in a pulse pattern in the human body and changes with the menstrual cycle in women. The main function of FSH is to make granulosa cells proliferate, endometrial cells differentiate, follicular fluid form and follicular cavity expand, so as to make follicle grow and develop, improve the effective rate of mature follicles, and then improve ovulation rate and pregnancy rate. Serum FSH levels are increased in patients with premature ovarian failure.

Female reproductive function is regulated through a positive and negative feedback mechanism of hormonal signals between the hypothalamic-pituitary-ovary, which becomes the "gonadal axis" and determines the ovarian cycle response and further determines the uterine cycle response. Decreased ovarian function or decreased ovarian reserve function, often accompanied by early increase in FSH in the ovarian follicles. This is due to the decrease in the secretory function of the ovary, and this change results in the need for the pituitary to secrete more stimulating hormones to improve the secretion of the ovary. The poor adaptive response of ovary leads to a compensatory increase in gonadotropin-releasing hormone (GnRH), which directly stimulates the pituitary secretion of FSH, resulting in an increase in FSH. It is generally believed that with the increase of FSH, the ovarian reserve is decreased, the ovarian response is poor, the number of developing follicles and oocytes are less, and the ovarian function is reduced.

The term "iatrogenic factor" used herein mainly includes ovarian dysfunction caused by surgery, radiotherapy and chemotherapy drugs, such as impairment of ovarian function.

The term "alkyl" used herein refers to fully saturated straight or branched non-aromatic hydrocarbons. Examples of straight and branched C1-C6 alkyl groups include methyl, ethyl, n-propyl, isopropyl, n-butyl, sec-butyl, tert-butyl, pentyl, hexyl, pentyl, and octyl.

"The term "alkenyl" used herein refers to a non-aromatic hydrocarbon containing at least one double bond.

"The term "alkynyl" used herein refers to a non-aromatic hydrocarbon containing at least one triple bond.

The term "pharmaceutically acceptable" used herein refers to the ability to be administered to humans and/or other animals as subjects without excessive adverse reactions or side effects (e.g., toxicity, irritation, anaphylaxis, etc.). The term "excipients" refers to auxiliary materials that are present in the pharmaceutical product at the same time as the active ingredient and do not produce excessive adverse reactions or side effects, including carriers, osmotic pressure regulators, pH regulators, diluents, disintegrants, excipients, solubilizers, stabilizers, preservatives, etc. The term "pharmaceutically acceptable excipients" refers to excipients with high safety that are suitable for a particular pharmaceutical product and are used routinely in pharmaceutical practice. The term "carrier", includes but is not limited to, liposomes, ethosomes, polymeric micelles, nanostructured lipid carriers, solid lipid nanocarriers, mesoporous silica nanoparticles, etc.

The term "pharmaceutically acceptable salt" used herein may include alkali metal salts (e.g., sodium or potassium salts), alkali earth metal salts (e.g., calcium salts or magnesium salts), and salts formed with suitable organic ligands (e.g., quaternary ammonium salts).

The term "HyodesoxycholicAcid (HDCA)" used herein was originally a cholan acid extracted from pig bile, which is a steroid acid mainly present in mammalian bile, and its chemical name is 3α, 6α-dihydroxy-5β-cholan acid. The differences between different bile acids are small, and the main differences are the presence or absence of hydroxyl groups at positions 3, 7, and 12. Bile acids are physiological cleaners that contribute to the powder, absorption, and transport of fats and steroids in the gastrointestinal tract and liver. Bile acids are also steroid amphipathic molecules derived from cholesterol metabolism, which regulate bile distribution and lipid secretion, are very important for the absorption of fat and vitamins in the diet, and participate in the regulation of the function of enzymes in cholesterol homeostasis. Bile acids are recycled through the liver-gut axis formed by the liver, bile ducts, small intestine, and portal vein. Studies have shown that Hyodeoxycholic acid can significantly reduce the cell necrosis rate and apoptosis rate of nerve cells in reoxygenation injury after hypoxia and glucose deprivation, and significantly increase the cell survival rate, indicating that Hyodeoxycholic acid has a significant anti-injury effect on nerve cells in reoxygenation after hypoxia or glucose deprivation. In addition, Hyodeoxycholic acid is a secondary hydrophilic bile acid formed by intestinal flora in the small intestine and can prevent gallstone formation in mice. Studies also have shown that Hyodeoxycholic acid not only inhibits intestinal cholesterol absorption, but also exerts other anti-atherosclerotic effects. HDCA has the effects of lowering blood lipids, antispasticity and expectoration. It can be clinically used in the treatment of hyperlipidemia, atherosclerosis, tracheitis, viral upper respiratory tract inflammation in children, and dyspepsia caused by hepatobiliary diseases. It has certain inhibitory effect on *Bordetella pertussis*, diphtheria bacillus, *Staphylococcus aureus* and so on.

The term "oestrous cycle" used herein, also known as the estrous cycle, refers to a frequent physiological change in the female that is present in placental mammals and is induced by sex hormones. The estrous cycle of a mouse or a rat is periodically repeated every 4 to 5 days. According to the follicular development and reproductive endocrine changes of the estrous cycle, the estrous cycle can be divided into proestrous, estrous, metestrum and diestrum. As an animal model to study the estrous cycle, mice or rats are widely used in experiments exploring the pathogenesis mechanism of female menstrual cycle related diseases, evaluating the effect of drugs and the development of corresponding drugs.

The term "prevention" used herein refers to the preventive treatment of a subclinical disease state aimed at reducing the probability of a clinical disease state occurring. "Prevention" can be divided into (a) primary prevention and (b) secondary prevention. Primary prevention was defined as the treatment of subjects who had not yet presented a clinical disease state, whereas secondary prevention was defined as the prevention of a second occurrence of the same or similar clinical disease state.

The term "treatment" used herein refers to the treatment of a disease, symptom or condition, including: 1) inhibition of the development of the disease, symptom or condition; and/or, 2) delay or relieve the disease, symptom or condition.

Biomarkers mentioned herein, such as follicle stimulating hormone (FSH), estrogen (e.g., E2), and superoxide dismutase (SOD), malondialdehyde (MDA), relative reactive oxygen species (ROS), and lactate dehydrogenase (LDH), etc., can be detected using methods commonly known in the field. Detection methods typically cover methods that quantify the level of a biomarker in a sample (quantitative methods). Which of the following methods are suitable for qualitative and/or quantitative detection of biomarkers is generally known to those skilled in the field. Samples can be conveniently measured, for example for proteins using immunoassays such as ELISA, RIA, etc., which are commercially available.

Embodiments and drawings are provided below to aid in the understanding of the invention. However, it should be understood that these embodiments and drawings are intended only to illustrate the invention and do not constitute any limitation. The actual scope of protection of the invention is set forth in the claims. It should be understood that any modifications and changes may be made without departure from the spirit of the invention.

EXAMPLES

Example 1. Preparation of Models of Premature Ovarian Insufficiency (POI) and Treatment With Sodium Fumarate and/or Hyodeoxycholic Acid Animal model establishment: A total of 34 C57 female mice (8-week-old) were selected and intraperitoneally injected with the ratio of 120 mg/kg cyclophosphamide (SIGMA) and 30 mg/kg Busulfan (Aladdin) once a day for 1 week at the dose of 0.1 mL/10 g to establish the model of POI.

Figure 1:
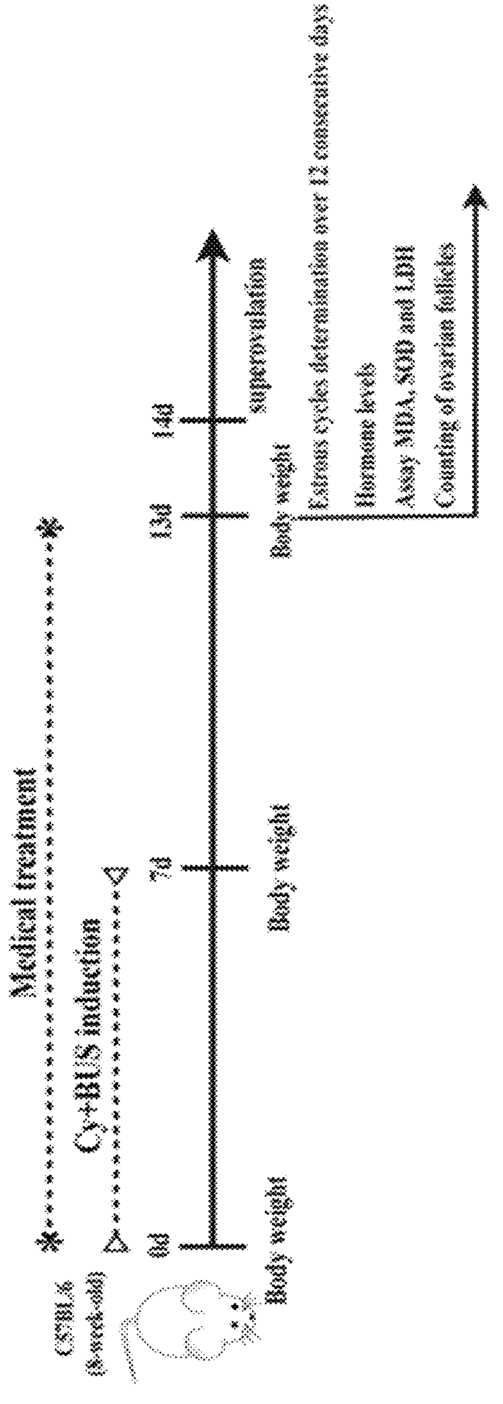
FIG. 1 shows the flow chart of drug administration and experimental design in mice.

Grouping: 34 POI model mice were randomly divided into four groups: sodium fumarate (SF) treatment group (n=9), hyodeoxycholic acid (HDCA) treatment group (n=8), sodium fumarate plus hyodeoxycholic acid (mass ratio 1:1) combination (SF+HDCA) treatment group (n=8) and normal saline (Vehicle) group (n=9). Mice in the SF group were given oral administration of SF at the ratio of 100 mg/kg/d body weight, mice in the HDCA group were given oral administration of HDCA at the ratio of 100 mg/kg/d body weight, and mice in the combination group were given oral administration of SF and HDCA at the ratio of 100 mg/kg/d body weight. SF and HDCA were dissolved with 0.9% normal saline when used. Mice in the vehicle group were given the same amount of normal saline orally. All the mice were treated consecutively for 12 days. FIG. 1 shows the schematic diagram of the experimental process.

Cytological observation of vaginal smear was performed daily.

The vagina of mice was exposed, and about 30 μl of normal saline was dripped into the vagina, gently aspirated onto the slide, and observed under the microscope. Staining was performed when necessary, fixed with 95% ethanol for 10 minutes, stained with hematoxylin in aqueous solution for 5-8 minutes, washed with running water for color separation, and then stained with eosin for 3 minutes. After drying. the slices were sealed with neutral gum.

Body weight were recorded at three time points, before modeling (at the beginning of treatment), after modeling and after treatment.

After 12 days of administration, half of the mice in each group were sacrificed, and their blood was collected and kept still. The serum was separated after centrifugation at 4500 rpm and stored in a refrigerator at −80° C. for future use to measure levels of follicle stimulating hormone, estrogen, and the indexes of oxidative stress such as superoxide dismutase (SOD) and malondial dehyde (MDA).

Example 2. Preparation of Models of Premature Ovarian Insufficiency (POI) and Treatment With Dimethyl Fumarate and/or Hyodeoxycholic Acid Animal model establishment: A total of 24 C57 mice (8-week-old) were selected and intraperitoneally injected with the ratio of 120 mg/kg cyclophosphamide and 30 mg/kg Busulfan once a day for 1 week at the dose of 0.1 mL/10 g to establish the model of POI.

Grouping: 24 POI model mice were randomly divided into four groups: dimethyl fumarate (DMF) treatment group (n=5), hyodeoxycholic acid (HDCA) treatment group (n=6), dimethyl fumarate plus hyodeoxycholic acid (mass ratio=1: 1) combination (DMF+HDCA) treatment group (n=7) and normal saline (Vehicle) group (n=6). Mice in the DMF treatment group were orally administrated at the ratio of 100 mg/kg/d body weight. Mice in the HDCA treatment group were given oral administration of HDCA at the ratio of 100 mg/kg/d body weight, and mice in the combination group were given oral administration of DMF and HDCA at the ratio of 100 mg/kg/d body weight. Once daily, DMF and HDCA were dissolved in 0.9% normal saline when used. Mice in normal saline group were given the same amount of normal saline orally every day. The drug was administered for 12 days. FIG. 1 shows the schematic diagram of the experimental process.

Cytological observation of vaginal smear was performed daily.

The vagina of mice was exposed, and about 30 μl of normal saline was dripped into the vagina, gently aspirated onto the slide, and observed under the microscope. Staining was performed when necessary, stained with hematoxylin in aqueous solution for several minutes after drying, washed with running water for color separation, and then stained with alchhol eosin for several seconds. The slices were sealed with neutral gum.

Body weight were recorded at three time points, before modeling (at the beginning of treatment, the 0th day), after modeling (the 7th day) and after treatment (the 13th day).

After 12 days of administration, half of the mice in each group were sacrificed, and their blood was collected and kept in still. The serum was separated after centrifugation at 4500 rpm and stored in a refrigerator at −80° C. for future use to measure levals of follicle stimulating hormone, estrogen, and the indexes of oxidative stress such as superoxide dismutase (SOD) and malondialdehyde (MDA).

Example 3. Results of Body Weight Measurement

The body weight of POI model mice of each group was measured before modeling, after modeling and after treatment.

The weight results of 34 mice in Example 1 are shown in Table 1 below.

TABLE 1

Body weight of each group of mice in Example 1 before modeling (D 0), after modeling (D 7), and after treatment (D 13)

| | Before modeling(g) | after modeling(g) | after treatment (g) |
|---|---|---|---|
| Vehicle | 19.66 ± 0.65 | 18.03 ± 1.45 | 17.87 ± 1.50 |
| SF | 18.77 ± 0.63 | 18.15 ± 0.92 | 18.07 ± 1.03 |
| HDCA | 18.79 ± 0.80 | 17.69 ± 1.03 | 17.96 ± 1.20 |
| SF + HDCA | 18.71 ± 0.75 | 17.89 ± 0.99 | 18.22 ± 0.75 |

Figure 2:
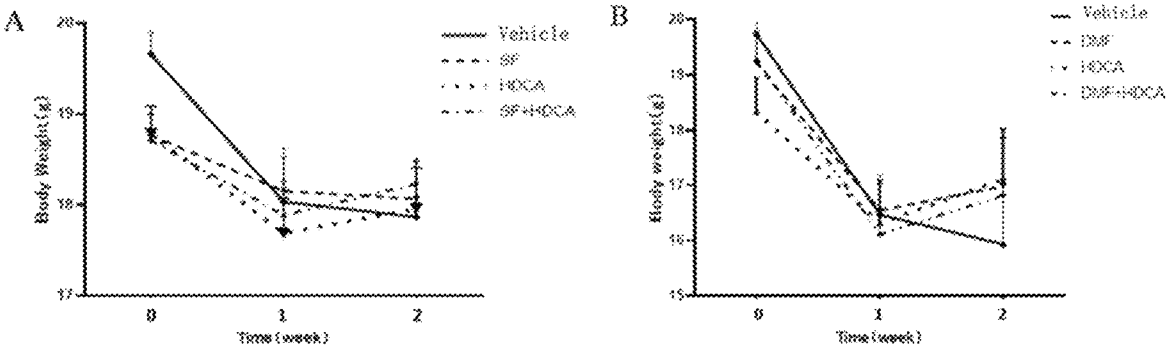
FIG. 2 shows the changes in body weight of mice before modeling, after modeling, and after treatment according to one embodiment. Among this.

Using Pillai's Trace analysis, intra-group comparison: The result of sphericity test P=0.004<0.05, the data did not meet the assumption of sphericity, so the result of multivariate analysis of variance should prevail. In Pillai's Trace analysis, the time P<0.05, and the interaction factors of time and group P>0.05, indicating that there were differences in the changes of body weight at different time points. In other words, the preparation of POI model drugs has an effect on body weight, and the effects of different treatment drugs on body weight will not be significantly different over time. Comparison between groups: ANOVA of different drug groups, P=0.851>0.05, indicating that there was no significant difference in body weight between different drug treatments. However, compound treatment of different treatment groups (SF, HDCA, and SF+HDCA) was significantly beneficial to weight recovery after chemotherapy, and the combination treatment group (SF+HDCA) was the most beneficial (FIG. 2A).

The weight results of 34 mice in Example 2 are shown in Table 2 below.

TABLE 2

Body weight of each group of mice in Example 2 before modeling (D 0), after modeling (D 7), and after treatment (D 13)

| | before modeling(g) | after modeling(g) | after treatment (g) |
|---|---|---|---|
| Vehicle | 19.73 ± 0.84 | 16.47 ± 1.37 | 15.93 ± 1.87 |
| DMF | 19.22 ± 1.39 | 16.54 ± 1.44 | 16.98 ± 1.99 |
| HDCA | 18.32 ± 1.61 | 16.31 ± 2.02 | 17.10 ± 2.24 |
| DMF + HDCA | 19.27 ± 1.26 | 16.11 ± 1.03 | 16.81 ± 2.40 |

Using Pillai's Trace analysis, intra-group comparison: The result of sphericity test P<0.05, the data did not meet the assumption of sphericity, so the result of multivariate analysis of variance should prevail. In Pillai's Trace analysis, the time P=0.015<0.05, and the two interaction factors of time and group P>0.05 suggested that there were differences in the changes of body weight at different time points. In other words, the modeling drugs had an effect on body weight, and the effects of different treatments (DMF, HDCA, and DMF+HDCA) on body weight did not differ significantly over time. Comparison between groups: ANOVA of different drug groups, P>0.05, indicating that there was no significant difference in body weight between different drug treatments. However, compound treatment of different treatment groups (SF, HDCA, and SF+HDCA) was significantly beneficial for weight recovery after chemotherapy (FIG. 2B).

Example 4. Observation of Estrous Cycles in Mice Modeled and Treated

During the estrous cycle, a series of histological and physiological changes occur in the reproductive and endocrine systems of mice. According to these changes, the estrous cycle can be divided into proestrous (P), estrous (E), metestrum (M) and diestrum (D).

1. Observation of estrous cycle in mice of Example 1

Figure 3:
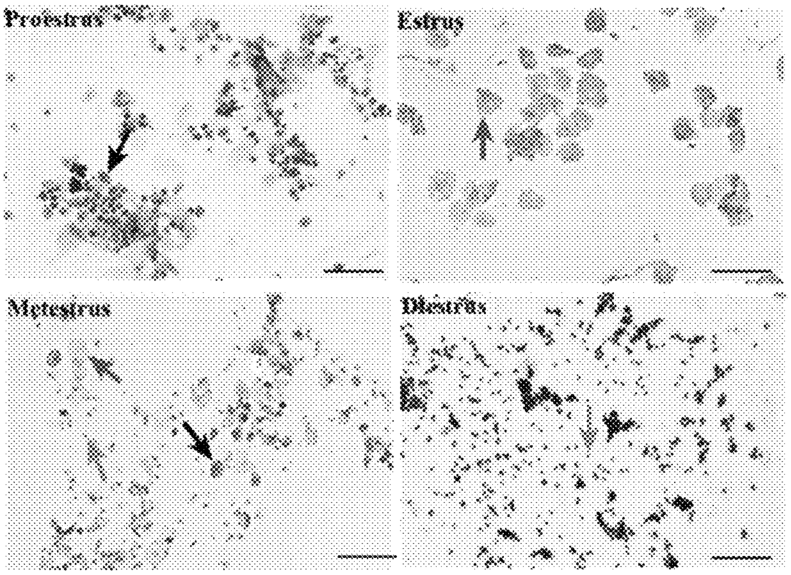
FIG. 3 illustrates the four periods of estrous cycle. Light gray arrows indicate leukocytes, dark gray arrows indicate keratinized epithelium, and black arrows indicate nucleated epithelium.

After modeling and treatment, there were 6 mice left in the normal saline group, 6 mice left in the sodium fumarate treatment group, 7 mice left in the hyodeoxycholic acid group, and 7 mice left in the sodium fumarate and hyodeoxycholic acid combination group. The estrous cycle of these mice was observed for 12 consecutive days. The estrous cycle was divided into four periods (P: proestrous; E: estrous period; M: metestrum; D: diestrum) for vaginal smear cytological observation, the results are shown in FIG. 3.

The estrous cycle of mice was plotted according to the cytological results of vaginal smears observed for 12 consecutive days, and the results are shown in FIG. 4. A representative estrous cycle diagram of mice from Embodiment 1 is shown in FIG. 4A. The estrous cycle of mice is about 4 to 5 days, which is divided into four periods alternately. If the estrous cycle diagram was showed "N", it indicates that the estrous cycle is regular or returns to normal. The results showed that 0 mice recovered estrous cycle in the normal saline group. The estrous cycle of 4 mice was recovered in sodium fumarate treatment group. The estrous cycle of 3 mice was recovered in HDCA group. The estrous cycle of 6 mice was recovered in group treated with SF and HDCA.

The proportion of each period of estrous cycle of mice in each group during drug administration was recorded, and the results are shown in FIG. 4B. See FIG. 4B:

For proestrous (P), the average rate in normal saline group was 29.17%; The average rate was 40.28% in SF treatment group and 23.81% in HDCA treatment group. The average rate of mice treated with SF and HDCA was 35.71%. There was a significant difference in the average rate between the SF treatment group and HDCA group (P<0.05), and there was a significant difference in the average rate between HDCA group and SF and HDCA combination group (P<0.05).

For estrous stage (E), the average rate of normal saline group was 6.94%; The average rate of mice in SF treatment group was 20.83%. The average rate of mice in HDCA group was 22.62%; The average rate of mice treated with SF and HDCA was 25%. The average rate was significantly different between the normal saline group and SF treatment group (P<0.05), the average rate was significantly different between normal saline group and HDCA group (P<0.05), and the average rate was significantly different between the normal saline group and SF and HDCA combination group (P<0.05).

For metestrum (M), the average rate of normal saline group was 12.50%; In the SF treatment group, the average rate was 18.10% in the metestrum period. In the HDCA group, the average rate was 14.29% in the metestrum period. In SF and HDCA combination group, the average rate was 13.10% in the metestrum period There was no significant difference in average rate among the groups in the metestrum period.

For diestrum (D), the average rate in normal saline group was 51.39%; The average rate of SF treated mice was 20.83%. The average rate of HDCA was 39.29%. The average rate of mice treated with SF and HDCA was 26.20%. There was a significant difference in the average rate between the normal saline group and the SF treatment group (P<0.01), there was a significant difference in the average rate between the normal saline group and the SF and HDCA combination group (P<0.01), and there was a significant difference in the average rate between the SF treatment group and the HDCA treatment group (P<0.01). These results indicate that SF, HDCA and the combination of SF and HDCA have preventive and therapeutic effects on mice with premature ovarian failure.

2. Observation of Estrous Cycle in Mice of Example 2

The estrous cycle of mice in Example 2 was observed for 12 consecutive days, and four periods of estrous cycle (proestrous (P), estrous (E), metestrum (M) and diestrum (D)) vaginal smear cytology was observed and estrous cycle graphs were drawn. FIG. 5A shows a representative estrous cycle diagram of Example 2. The statistical results showed that estrous cycle was recovered in 1 mouse in the control group (n=6), 4 mice in the dimethyl fumarate (DMF) treatment group (n=5), 3 mice in the HDCA group (n=6), and 3 mice in the combined DMF and HDCA group (n=7).

The proportion of each period of estrous cycle in each group of mice during drug administration was recorded, and the results are shown in FIG. 5B. See FIG. 5B:

For proestrous (P), the average rate of control mice was 14.58%; In the DMF treatment group, the average rate was 27.50%. In HDCA treatment group, the average rate was 29.17%. The average rate of mice treated with DMF and HDCA was 17.86%. There were significant differences in the average rate between the control group and the HDCA treatment group (P<0.05).

For estrous (E) stage, the average rate of control mice was 12.50%; The average rate of mice treated with DMF was 15.00%. The average rate of mice in HDCA treatment group was 6.25%. The average rate of mice treated with DMF and HDCA was 16.07%. There were no significant differences in average rate among the groups.

For the metestrum (M), the average rate of control group was 16.67%; In the DMF treatment group, the average rate was 2.50%. In the HDCA group, the average rate was 12.50%. The average rate of mice treated with DMF and HDCA was 8.93%. There was a significant difference in the average rate between the control group and the DMF treatment group (P<0.05).

For the diestrum (D), the average rate of control mice was 56.25%; In the DMF treatment group, the average rate was 55.00%. The average rate of HDCA group was 52.08%. The average rate of mice treated with DMF and HDCA was 57.14%. There were no significant differences in the average rate among the groups. These results indicate that DMF, HDCA and their combination have preventive and therapeutic effects on mice with premature ovarian failure.

Example 5. Results of Determination of Serum Hormone Levels

1. Hormone levels in mice blood of Example 1 are measured in this embodiment. Measurements of serum hormone levels are shown in Table 3, FIGS. 6 and 7.

TABLE 3

Effect of sodium fumarate and hyodeoxycholic acid on serum hormones in POI mice

| | FSH (mIU/mL) | $E_2$ (pg/mL) |
|---|---|---|
| Vehicle | 7.67 ± 2.04 | 41.35 ± 5.14 |
| SF | 8.56 ± 2.59 | 57.24 ± 4.56 |
| HD | 4.85 ± 2.34 * | 49.69 ± 7.11 |
| SF + HD | 2.76 ± 1.14 ** | 41.70 ± 14.45 |

As shown in FIG. 6, compared with the normal saline group which as the control, the serum FSH levels of the HDCA treatment group, SF and HDCA combined treatment group showed a decreasing trend, and the differences were statistically significant (HDCA treatment group P=0.049, P<0.05; SF and HDCA combined group P=0.002, P<0.01). Compared with the normal saline group, the serum FSH level in the SF treatment group showed a certain increasing trend, but the difference was not statistically significant. Compared with the SF treatment group, the level of FSH in the HDCA treatment group and the SF and HDCA combined group showed a significant tendency to decrease, and the difference was statistically significant (the HDCA treatment group P=0.013, P<0.05; SF and HDCA combined group P<0.0001). The serum FSH level of the SF treatment group showed a certain increasing trend, but the difference was not statistically significant. This indicates that HDCA or the combination of SF and HDCA has the effect of reducing serum FSH. Among them, the combination of SF and HDCA had the best effect. Therefore, HDCA has significant effect of decreasing serum FSH levels, and SF also has certain effect of decreasing serum FSH levels.

As shown in FIG. 7, after treatment, serum E2 levels were measured, and compared with the normal saline group, serum E2 levels showed a tendency to increase in the SF treatment group, the HDCA treatment group, and the SF and HDCA combined treatment group. This indicates that SF, HDCA or the combination of SF and HDCA has the effect of increasing serum E2 levels.

2. Hormone levels in blood of mice of Example 2 are measured in this embodiment. Table 4 and FIG. 8 show the results of measurements of serum hormone levels.

TABLE 4

Effect of dimethyl fumarate and hyodeoxycholic acid on serum hormones in POI mice

| | FSH (mIU/mL) | $E_2$ (pg/mL) |
|---|---|---|
| Vehicle | 4.04 ± 1.92 | 58.85 ± 10.34 |
| DMF | 2.39 ± 1.07 | 48.86 ± 11.41 |
| HDCA | 1.65 ± 0.76 | 42.96 ± 14.28 |
| DMF + HDCA | 5.62 ± 4.20 | 44.19 ± 5.27 |

Compared with the normal saline group, the serum FSH level of the dimethyl fumarate (DMF) treatment group and the hyodeoxycholic acid (HDCA) treatment group showed a certain decreasing trend, and the dimethyl fumarate and hyodeoxycholic acid combination group (DMF+HDCA) showed a certain increasing trend, but the difference between the groups was not statistically significant.

Compared with the normal saline group, the serum E2 level of DMF treatment group, HDCA treatment group, DMF+HDCA treatment group showed a certain tendency to decrease, but the difference between the groups was not statistically significant.

Example 6. Determination of Oxidative Stress Levels

The oxidative stress hypothesis believes that the reduction of antioxidant components in the body leads to the weakening of the ability to remove free radicals, which leads to oxidative damage of biological macromolecules, and the imbalance of cellular oxidative and antioxidant functions, which leads to oxidative stress, and then leads to disease and aging. Oxygen free radicals act on unsaturated fatty acids of lipids to generate lipid peroxides, including malondialdehyde (MDA) and so on. The antioxidant defense system of scavenging free radicals includes superoxide dismutase (SOD) and so on. Recently, oxidative stress has been reported to be associated with ovarian aging and POI in primates. Therefore, this embodiment examined the effects of DMF, HDCA, and DMF+HDCA on oxidative stress in mice with premature ovarian failure, and the results are shown in Table 5, FIGS. 9 to 12.

TABLE 5

Comparison of oxidative stress indicators after medical treatment

| | SOD (U/mL) | MDA (nmol/mL) | ROS |
|---|---|---|---|
| Vehicle | 5.13 ± 2.47 | 5.58 ± 2.49 | 7.631 ± 1.418 |
| DMF | 14.42 ± 9.05 | 1.83 ± 3.06 | 4.610 ± 0.476 |
| HDCA | 14.59 ± 5.65 | 2.86 ± 4.39 | 4.589 ± 0.599 |
| DMF + HDCA | 14.27 ± 3.87 | 0.10 ± 5.93 | 4.278 ± 0.374 |

As shown in FIG. 9, after treatment, the activity of SOD was increased in the DMF treatment group, the HDCA treatment group, and the DMF and HDCA combination group compared with the normal saline group, although the difference was not significant. This indicated that the serum SOD enzyme level and antioxidant capacity of POI mice were increased after treatment of DMF, HDCA, and the combination of DMF and HDCA.

As shown in FIG. 10, after treatment, serum MDA levels were measured. Compared with the normal saline group, MDA activity was reduced to some extent in the DMF treatment group, the HDCA treatment group, and the DMF and HDCA combination group, but there was no significant difference. The combination of DMF and HDCA showed the best reduction effect, followed by DMF treatment group, but there was no significant difference among the administration groups.

As shown in FIG. 11, after treatment, the relative reactive oxygen species (ROS) levels in serum were measured, among which the normal saline group had the highest ROS level, while compared with the normal saline group, the ROS levels in DMF group, HDCA treatment group, and the DMF and HDCA combined treatment group were significantly reduced.

As shown in FIG. 12 and Table 6, the activity of lactate dehydrogenase (LDH) was reduced to some extent in the SF treatment group, the HDCA treatment group, and the SF+HDCA combined treatment group compared with the normal saline group. Among them, SF group and SF+HDCA group had the best reduction effect, followed by HDCA group.

TABLE 6

Comparison of oxidative stress indicators after medical treatment

| | LDH (U/mL) |
|---|---|
| Vehicle | 3471.57 ± 662.67 |
| SF | 3136.09 ± 294.67 |
| HDCA | 2821.58 ± 318.30 |
| SF + HDCA | 1888.62 ± 242.49 |

Example 7. Effect of Sodium Fumarate and Hyodeoxycholic Acid on Ovulation in Mice With Premature Ovarian Failure In this Embodiment, the effect of sodium fumarate and hyodeoxy cholic acid on ovulation in aged mice with ovarian dysfunction (ovarian function decline due to natural aging) was examined. Fourteen months old mice were divided into three groups: control group (n=6), sodium fumarate group (SF, n=4), sodium fumarate and hyodeoxy cholic acid group (SF+HDCA, n=3).

Methods: After controlled ovarian hyperstimulation (48 hours after pregnant horse serum injection, followed by chorionic gonadotropin injection), the ampulla of fallopian tubes of mice was collected 14-16 hours later, and the number of oocytes obtained was recorded. The results are shown in FIGS. 13 and 14. As shown in FIG. 13, in the control group (C), one mouse ovulated and 5 mice did not ovulate. All 4 mice in the SF group ovulated. Two mice ovulated and one did not ovulate in the SF+HDCA group. SPSS Chi-square test (Fisher's exact test) showed significant differences. This indicates that sodium fumarate, or sodium fumarate and hyodeoxycholic acid combination, can restore ovulation in aged mice.

Example 8. Effect of Dimethyl Fumarate, Hyodeoxycholic Acid, and Dimethyl Fumarate Plus Hyodeoxycholic Acid on Gene Expression Mice were sacrificed after various treatments, and ovarian tissues were taken, snap-frozen in liquid nitrogen, stored at −80° C., and sent to Annoroad for RNA transcription level sequencing. Bioinformatics analysis and mapping were performed on the sequencing results. The RNA levels of the dimethyl fumarate treatment group, the hyodeoxycholic acid treatment group, and the dimethyl fumarate and hyodeoxycholic acid combination group were compared with the normal saline group, and the significantly differentially expressed genes were found (the fold change was >2 or >10, corrected P value <0.05). The differential genes of the three treatment groups were intersectioned. Differential gene sets (FC>2, Q<0.05) that were jointly up-regulated or down-regulated in the three treatment groups were obtained (FIG. 15). These differential gene sets were then subjected to Gene Ontology function (GO) enrichment (FC>2, Q<0.05) (FIG. 16) and signaling pathway (KEGG) analysis mapping (FIG. 17), respectively.

Compared with the control group, 1547, 1898, 1809 genes were up-regulated in the three treatment groups (DMF, HDCA, DMF+HDCA), respectively, and 620 genes were jointly up-regulated; 5261, 4749 and 4738 genes were down-regulated, respectively, and 3431 genes were jointly down-regulated, and 1339 genes were down-regulated more than 10 folds. Functional enrichment analysis was performed on genes that were up-regulated by 2 folds and down-regulated by more than 10 folds, respectively. The up-regulated genes were mainly related to Oxidation-reduction, NAD binding and other functions, and the down-regulated genes were mainly related to calcium and iron ion binding and channel activity etc. The results of signal pathway enrichment showed that the expression of genes in metabolism and steroidogenesis pathways was up-regulated after treatment; while he gene expressions of arachidonic acid metabolism, oleic acid metabolism, retinol signaling pathway and hippo signaling pathway were significantly down-regulated.

The technical solutions of the present invention is not limited to the limitations of the above specific embodiments, and any technical deformation made according to the technical solutions of the present invention falls within the scope of protection of the present invention.

The invention claimed is:

1. A method of treatment or prevention of ovarian dysfunction diseases comprising administering a compound of Formula I or a pharmaceutically acceptable salt thereof Formula I

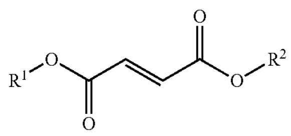

wherein: R1 and R2 are each independently selected from H, C1-C6 alkyl group, C1-C6 alkenyl group or C1-C6 alkyne group;

administering hyodeoxycholic acid or its pharmaceutically acceptable salt; and wherein the ovarian dysfunction diseases are treated.

2. The method of claim 1, wherein R1 and R2 are each independently selected from the H or C1-C6 alkyl groups.

3. The method of claim 1, wherein the ovarian dysfunction diseases is selected from the group consisting of premature ovarian insufficiency, premature ovarian failure, diminished ovarian reserve, poor ovarian response, early menopause, impaired ovarian function, insufficient ovarian function, lowered ovarian function.

4. The method of claim 1, wherein the ovarian dysfunction disease is caused by genetic factors, iatrogenic factors, immunologic factors, environmental factors, physical advanced age, and a combination thereof.

5. The method of claim 1 wherein the compound shown in Formula I or a pharmaceutically acceptable salt thereof is administered simultaneously or sequentially with hyodeoxycholic acid or a pharmaceutically acceptable salt thereof.

6. A composition for the prevention or treatment of ovarian disorders, which is characterized in that wherein the composition comprises a compound of Formula I or a pharmaceutically acceptable salt thereof, and hyodeoxycholic acid and a pharmaceutically acceptable salt thereof, Formula I

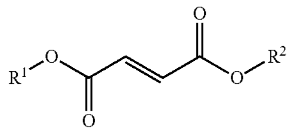

wherein R1 and R2 are each independently selected from H, C1-C6 alkyl group, C1-C6 alkenyl group or C1-C6 alkyne group; and hyodeoxycholic acid; and a pharmaceutically acceptable excipient.

7. The composition of claim 6, wherein R1 and R2 are each independently selected from H or C1-C6 alkyl groups.

8. The composition of claim 6, wherein the composition is in the form of a tablet, capsule, solution, granule, pill, powder, ointment, elixir, suspension, dust, injection, suppository, cream, spray or patch.

9. The method of claim 1, wherein R1 and R2 are each independently selected from the H or C1-C5 alkyl groups.

10. The method of claim 1, wherein R1 and R2 are each independently selected from H, methyl, ethyl, n-propyl, isopropyl, n-butyl, sec-butyl, tert-butyl, and n-pentyl groups.

11. The method of claim 3, wherein further comprises the administration of hyodeoxycholic acid or its pharmaceutically acceptable salt to relieve oxidative stress damage, restore sex hormone secretion, and restore ovulation.

12. The composition of claim 7, wherein R1 and R2 are each independently selected from the H or C1-C5 alkyl groups.

13. The composition of claim 11, wherein R1 and R2 are each independently selected from H, methyl, ethyl, n-propyl, isopropyl, n-butyl, sec-butyl, tert-butyl, and n-pentyl groups.

* * * * *